(12) United States Patent
Bornemann

(10) Patent No.: US 9,505,000 B2
(45) Date of Patent: Nov. 29, 2016

(54) DEVICE FOR CELL SPRAYING, MANUFACTURING OF THE DEVICE, METHOD FOR SPRAYING WITH THE DEVICE AND A CELL SUSPENSION SPRAYED WITH THE DEVICE

(75) Inventor: Reinhard Bornemann, Bielefeld (DE)

(73) Assignee: RenovaCare Sciences Corp., New York, NY (US)

( * ) Notice: Subject to any disclaimer, the term of this patent is extended or adjusted under 35 U.S.C. 154(b) by 932 days.

(21) Appl. No.: 13/573,003

(22) Filed: Aug. 13, 2012

(65) Prior Publication Data

US 2013/0060335 A1   Mar. 7, 2013

(51) Int. Cl.
| | |
|---|---|
| *A61F 2/10* | (2006.01) |
| *B01L 3/02* | (2006.01) |
| *C12M 1/26* | (2006.01) |
| *A61M 35/00* | (2006.01) |

(52) U.S. Cl.
CPC ............. *B01L 3/0255* (2013.01); *C12M 33/04* (2013.01); *A61M 35/00* (2013.01); *B01L 2200/0631* (2013.01); *B01L 2300/0838* (2013.01); *B01L 2300/163* (2013.01); *B01L 2400/0487* (2013.01)

(58) Field of Classification Search
CPC .. C12M 33/04; A61M 35/00; A61M 35/003; A61M 11/00; A61M 11/02; B01L 3/0255; B01L 2200/0631; B01L 2300/163; B01L 2300/0838; B01L 2400/0487
See application file for complete search history.

(56) References Cited

U.S. PATENT DOCUMENTS

| | | |
|---|---|---|
| 5,139,031 A | 8/1992 | Guirguis |
| 5,571,083 A | 11/1996 | Lemelson |
| 5,810,885 A * | 9/1998 | Zinger ................... A61C 5/064 604/197 |
| 6,117,150 A * | 9/2000 | Pingleton ............... A61B 17/00 604/35 |
| 6,479,052 B1 | 11/2002 | Marshall et al. |
| 7,628,780 B2 | 12/2009 | Bonner et al. |
| 7,641,898 B2 | 1/2010 | Lyles |

(Continued)

FOREIGN PATENT DOCUMENTS

| | | |
|---|---|---|
| DE | 102007040252 A1 | 6/2008 |
| DE | 102011100450 A1 | 10/2012 |

(Continued)

OTHER PUBLICATIONS

Bionumbers Database, Key Numbers for Cell Biologists, posted Aug. 26, 2010, available online as of Feb. 8, 2016 at http://book.bionumbers.org/how-big-is-an-e-coli-cell-and-what-is-its-mass/.*

(Continued)

*Primary Examiner* — Theodore Stigell
*Assistant Examiner* — Amber Stiles
(74) *Attorney, Agent, or Firm* — Schwegman Lundberg & Woessner, P.A.

(57) ABSTRACT

The invention provides a description of a method and a device suitable for producing a cell suspension spray with living cells, and the produced cell preparation, suitable for grafting to a patient. In contrast to other methods, the spraying is performed through a disposable needle which is inserted into a disposable air tube; which provides a cell distribution avoiding spray nozzles. Small suspension droplets are provided instead of cell nebulization. By using medical grade sterile Luer-lock disposables from medical routine praxis, biocompatibility and easy application is addressed. In applying the method and/or in using the device, cells suitable for grafting to a patient are dispersed in a solution and sprayed with the device for distribution over the recipient graft site.

19 Claims, 3 Drawing Sheets

(56) References Cited

U.S. PATENT DOCUMENTS

Figure 1:
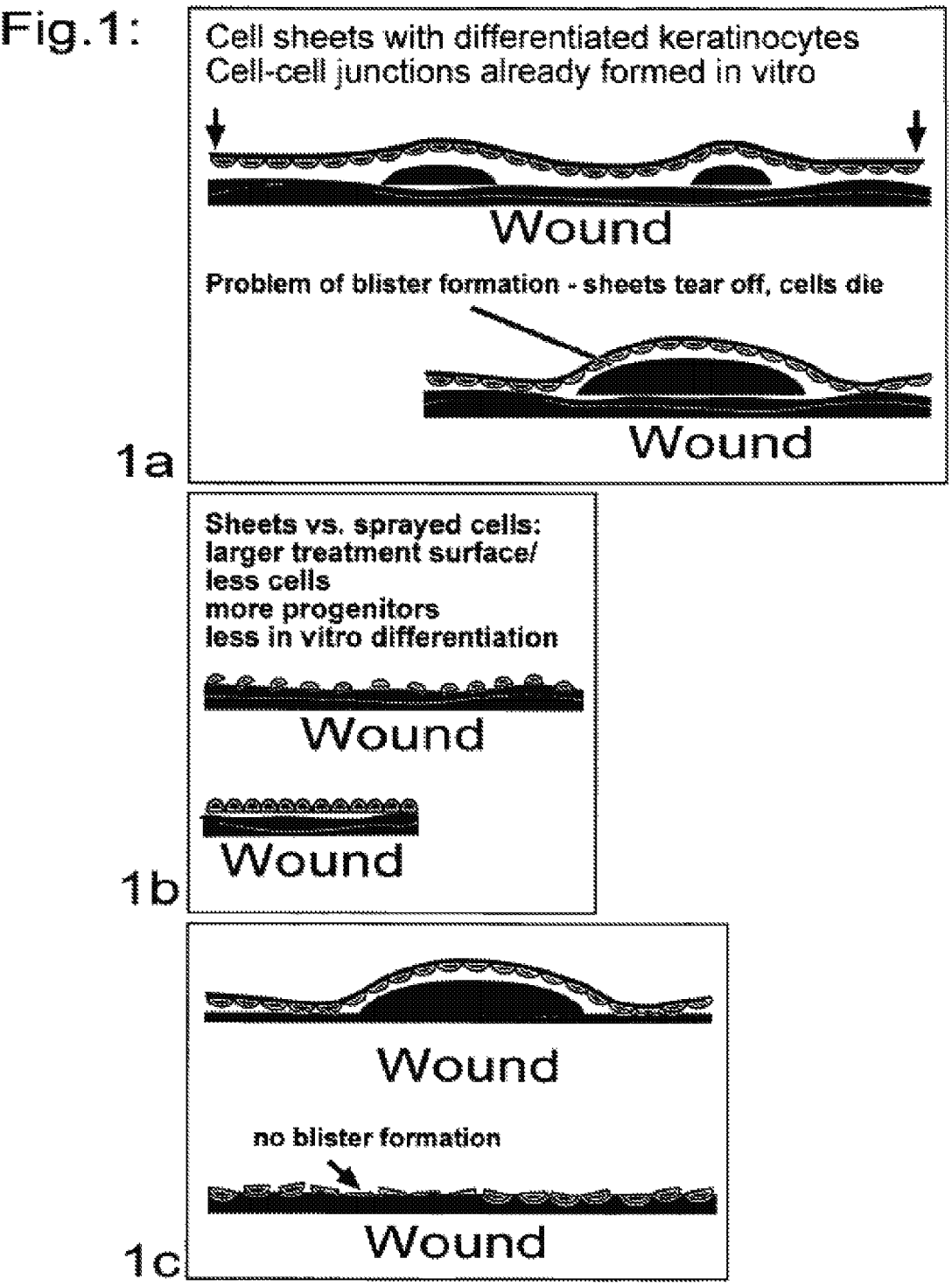
Figure 2:
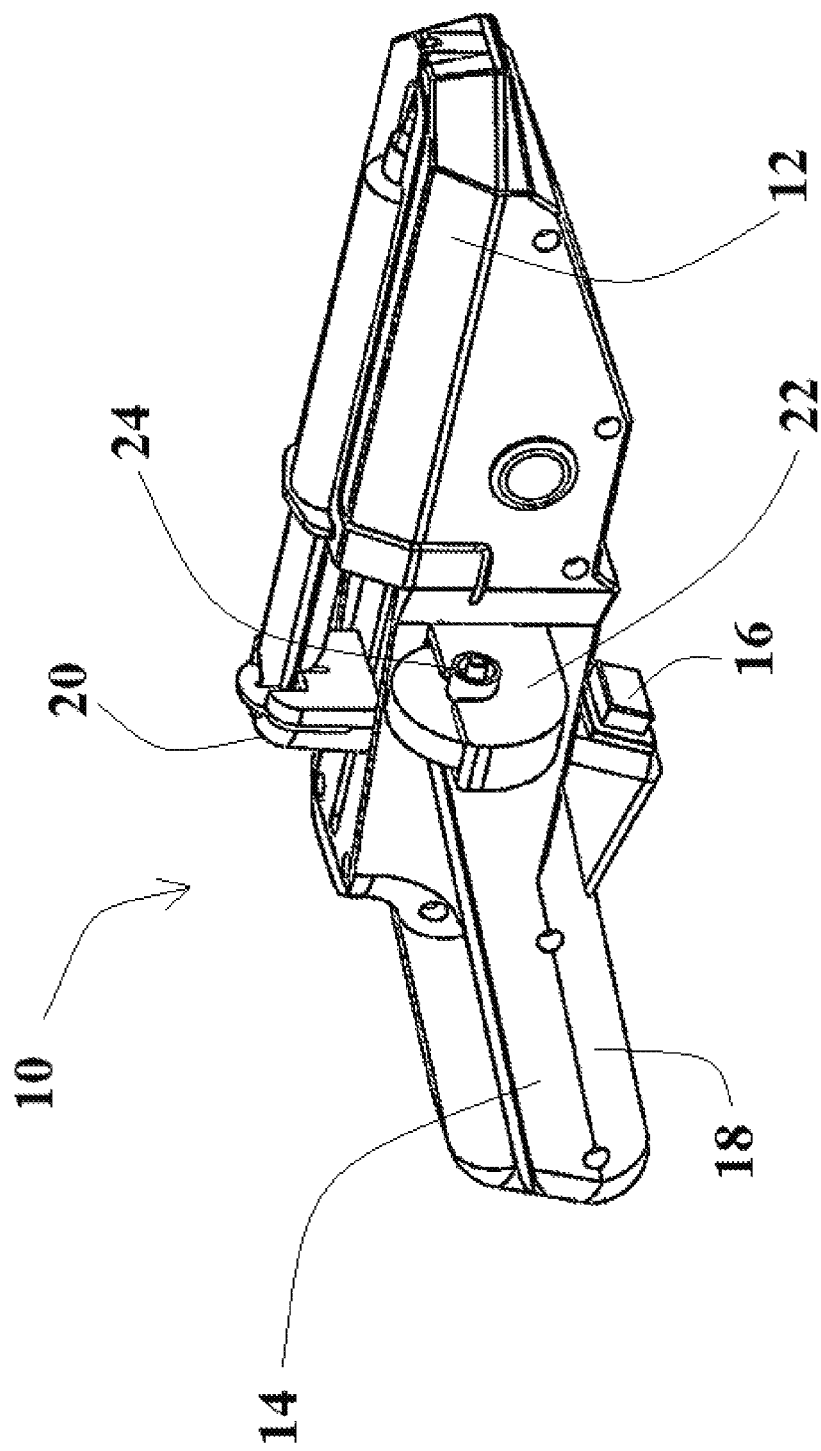
Figure 3:
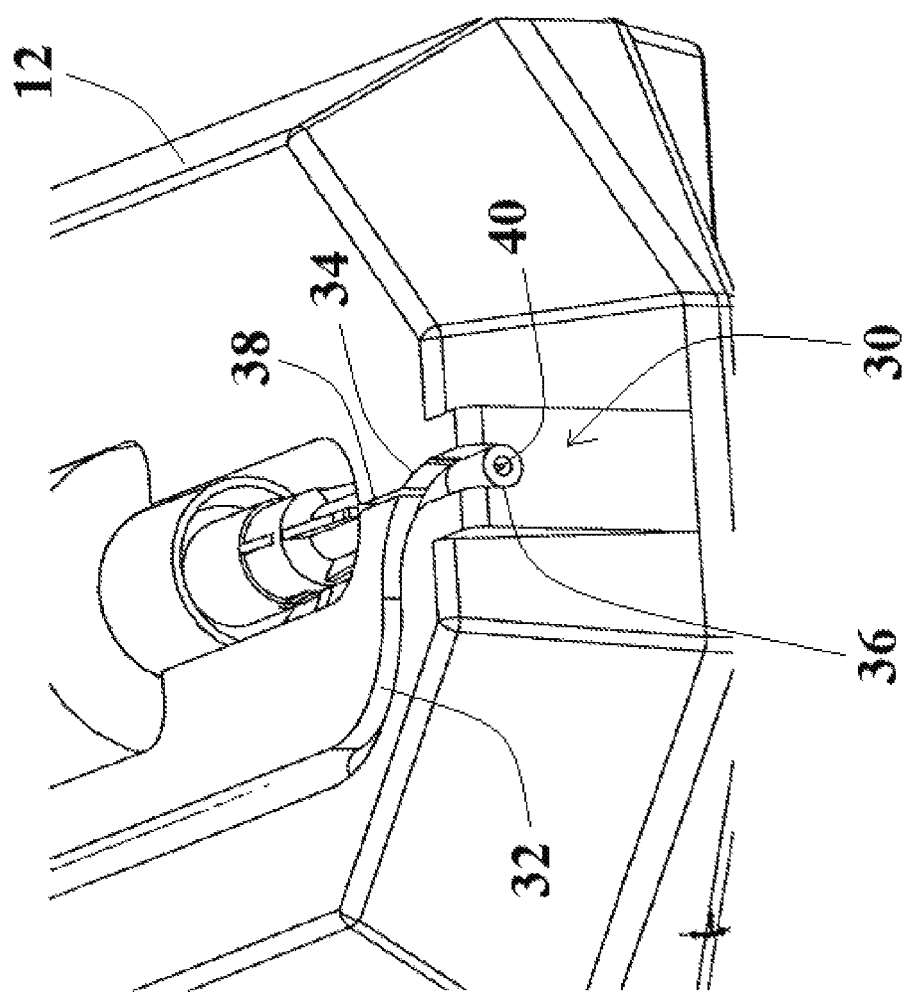

| | | | |
|---|---|---|---|
| 8,157,817 | B2 | 4/2012 | Bonadio et al. |
| 2002/0082692 | A1 | 6/2002 | Van Blitterswijk et al. |
| 2002/0106353 | A1 | 8/2002 | Wood et al. |
| 2003/0202965 | A1 | 10/2003 | Seubert et al. |
| 2004/0043007 | A1 | 3/2004 | Andree et al. |
| 2004/0185091 | A1* | 9/2004 | Truong-Le ....... A61K 39/39591 424/450 |
| 2004/0219133 | A1 | 11/2004 | Lyles |
| 2007/0042488 | A1* | 2/2007 | Bornemann ............ A61F 2/105 435/284.1 |
| 2008/0038298 | A1* | 2/2008 | Barnikol-Keuten . A61K 9/1075 424/400 |
| 2009/0191631 | A1 | 7/2009 | Bornemann |
| 2009/0196855 | A1 | 8/2009 | Bornemann |

FOREIGN PATENT DOCUMENTS

| | | | |
|---|---|---|---|
| DE | 102011100450 | B4 | 7/2013 |
| DE | 102011100450 | B8 | 10/2013 |
| EP | 0809976 | A2 | 12/1997 |
| EP | 1357922 | B1 | 5/2011 |
| WO | WO-02062358 | A1 | 8/2002 |

OTHER PUBLICATIONS

"U.S. Appl. No. 11/518,012, Final Office Action mailed Jun. 21, 2013", 15 pgs.

"U.S. Appl. No. 11/518,012, Non Final Office Action mailed Aug. 7, 2007", 9 pgs.

"U.S. Appl. No. 11/518,012, Notice of Non-Compliant Amendment mailed Jan. 29, 2013", 3 pgs.

"U.S. Appl. No. 11/518,012, Response filed Feb. 28, 2013 to Notice of Non-Compliant Amendment mailed Jan. 29, 2013", 10 pgs.

"U.S. Appl. No. 11/518,012, Response filed Dec. 22, 2011 to Non Final Office Action mailed Aug. 7, 2007", 13 pgs.

"U.S. Appl. No. 14/136,681, Preliminary Amendment mailed Apr. 21, 2014", 8 pgs.

"Skin Cell Gun", Wikipedia, [Online]. Retrieved from the Internet: <URL: http://en.wikipedia.org/wiki/Skin_cell_gun>, (Accessed Apr. 22, 2014), 5 pgs.

Gerlach, "Skin Cell Gun", Poster, [Online]. Retrieved from the Internet: <URL: http://bethsumner.com/wp-content/uploads/2012/05/1338405697mmvrposter.jpg>, (2012), 1 pg.

Gerlach, Jorg C, et al., "Method for autologous single skin cell isolation for regenerative cell spray transplantation with non-cultured cells", Int J Artif Organs 34(3), 271-279.

Hartmann, Bernd, et al., "Sprayed cultured epithelial autografts for deep dermal burns of the face and neck", Ann Plast Surg. 58(1), (2007), 70-73.

Herndon, David N, et al., "Comparison of cultured epidermal autograft and massive excision with serial autografting plus homograft overlay", J Burn Care Rehabil 13(1), (1992), 154-157.

Johnen, C., et al., "Skin cell isolation and expansion for cell transplantation is limited in patients using tobacco, alcohol, or are exhibiting diabetes mellitus", Burns, 32(2), (Mar. 2006), 194-200.

Navarro, F. A, et al., "Sprayed Keratinocyte Suspensions Accelerate Epidermal Coverage in a Porcine Microwound Model", Journal of Burn Care & Rehabilitation, 21(6), (Nov./Dec. 2000), 513-518.

Wood, Fiona, "Clinical Potential of Autologous Epithelial Suspension", Wounds 15(1), (2003), 16-22.

"U.S. Appl. No. 14/136,681, Non Final Office Action mailed Aug. 25, 2015", 10 pgs.

"Respiratory Failure and Stimulation of Glycolysis in Chinese Hamster Ovary Cells Exposed to Normobaric Hyperoxia*", The Journal of Biological Chemistry 265(19), (1990), 11118-11124.

Balin, Arthur K, et al., "Oxygen modulates growth of human cells at physiologic partial pressures", The Journal of Experimental Medicine 160(1), (Jul. 7, 1984), 152-166.

Goetz, Ingeburg E, "Oxygen Toxicity in Normal and Neoplastic Hamster Cells in Culture", Society for inn Vitro Biology 11(6), (1975), 382-394.

Kazzaz, Jeffery A, et al., "Cellular Oxygen Toxicity. Oxidant Injury Without Apoptosis*", The Journal of Biological Chemistry 271(25), (1996), 15182-15186.

Michiels, Carine, et al., "Comparative Study of Oxygen Toxicity in Human Fibroblasts and Endothelial Cells", Journal of Cellular Physiology 144(2), (Aug. 1990), 295-302.

U.S. Appl. No. 14/136,681, Final Office Action mailed Jun. 1, 2016, 11 pgs.

U.S. Appl. No. 14/136,681, Response filed Feb. 23, 2016 to Non Final Office Action mailed Aug. 25, 2015, 15 pgs.

* cited by examiner

DEVICE FOR CELL SPRAYING, MANUFACTURING OF THE DEVICE, METHOD FOR SPRAYING WITH THE DEVICE AND A CELL SUSPENSION SPRAYED WITH THE DEVICE

FIELD OF THE INVENTION

This invention relates to a technique for the deposition of cells, in particular to a device for spraying a cell suspension and distributing that cell suspension on a surface, e.g. in biomedicine, or a wound surface.

DESCRIPTION OF THE PRIOR ART

Spraying of cells may be of interest for the distribution of cell suspensions onto a surface, e.g. in biomedical research, or onto a tissue wound, or onto a skin wound. This can be applied, e.g., in general surgery to help regenerate tissue trauma or burns.

There are many methods for treating skin wounds known to those skilled in the art. For example, skin grafting techniques exist, which aim to reconstruct skin areas of the body that have suffered either damage or defects to the skin. In general, these types of grafts are classified according to their host-donor relationship and by their thickness. The most clinically applied graft is the autologous graft, whereby tissue is taken from one area of the body and applied to another area. The grafted tissue then develops a new blood supply and attaches to the underlying tissues. There are several types of skin grafts presently used, including split-thickness, full-thickness grafts, and micro-grafting. Each of these graft types must be prepared using certain techniques, and each one has its inherent advantages and disadvantages. Split-thickness grafts often require considerable skill, time and expensive equipment. Further, donor sites are as large as the treatment sizes and consequently painful, result in scarring and limit the coverable area. Although split-thickness grafts may be more successful than full-thickness grafts, they are usually cosmetically less attractive. Full-thickness grafts require less skill or expensive equipment, and their cosmetic appearance is better than that of split-thickness grafts. However, full-thickness grafts do not "take" as well as split-thickness grafts.

An alternative to split-skin grafting is to form a blister under suction at a donor site, then remove the skin above the blister and transplant it onto the recipient site. The production of blisters to treat wounds has been used since the 1960s. The blisters are produced by a suction device, such as Dermavac™, at a suction pressure of approximately 250-300 mmHg for 1-2 hours. The blisters are then cut off and placed on the wound. The healing time is around 10-14 days. There are several disadvantages to this method such as the amount of time required to prepare the graft is too long and the graft may not result in re-pigmentation of the area; or uneven pigmentation is common around the edges of the area of treatment.

Micro-grafting has become a more common approach for large area cover and involves the "snipping off" of a number of very small sections of tissue from a donor site and applying them to a dressing that is applied to the wound area. Micro-grafts are more easily accomplished and require no special instruments. However, their cosmetic appearance is not as good as other techniques, as the resulting scarring is often not acceptable.

A variation to the above grafting techniques is the mesh graft, which is a type of split-thickness or full-thickness skin graft in which parallel rows of slits are cut into the treated tissue. Some of the advantages of mesh grafts include: greater coverage of the effected area, drainage of blood or serum from beneath the graft, and increased conformity of the graft to uneven recipient areas. This technique has been very successful, with high "take" rates after the grafts have been applied on healthy granulation beds.

In the development of transplantation methods the size of the transplanted units there is a trend towards smaller and smaller units, as described below up to the level of single cells. Also, the size of the donor area can be consequently more and more reduced.

A further technology for the generation of tissue is the in vitro culture of epidermis cells. Cultured epithelial autografts (CEA), provided in confluent grown cell sheets, are an important adjunct in the coverage of burns and other situations in which large areas of the body's surface experience skin loss. There are many centres throughout the world with tissue culture facilities whose aim is to produce autologous epithelial grafts for use in a wide variety of applications; see Navarra et al. (2000) and Jihnen et a. (2006). The usefulness and application of CEA is related to its ability to achieve confluent cells sheets suitable for grafting. This technique overcomes many of the disadvantages of the previous treatments described above. For example, cultured epithelial autografts reduce the demand for donor sites. However, these autografts are slow growing and require time to culture, which often exceeds the preparation time of the recipient's sites. Moreover, blister formation by wound secretion below the sheet grafts hinder grafting. Navarro et al. (2000) and Wood et al. (2003) describe the use of single cells suspended in solution and distributed over the wound, thus avoiding the sheets. The cell suspension may be delivered via the use of a pipette, common "eye-droppers," syringe and needle, and/or other similar devices to place small quantities of cellular suspension on a graft site. As method of choice a mechanical hand driven spray technique is described and a kit "ReCellkit" is offered (see references of Wood et al.).

The spray technique addresses some afore mentioned problems in the field. A hand driven spray method and subsequently the distribution of the cells, however, is not performed in a controlled manner and results in uneven cell distribution.

The present invention provides a device, methods to manufacture the device, methods to distribute cells and the cell suspension generated by using the method, each of which seeks to ameliorate some of the disadvantages associated with prior art CEA grafting technology.

SUMMARY OF THE INVENTION

The present invention provides a device, the methods for manufacturing the device, methods for generating a cell suspension suitable for producing a transplantable cellular spray of living cells suitable for grafting to a patient and methods for cell spraying. In contrast to other methods, the spraying is performed through a disposable needle which is inserted into a disposable air tube; which provides a cell distribution avoiding spray nozzles. Small suspension droplets are provided instead of cell nebulization. By using medical grade sterile Luer-lock disposables from medical routine praxis, biocompatibility and easy application is addressed In applying the method and/or in using the device, cells suitable for grafting to a patient are dispersed in a solution and sprayed with the device for distribution over the recipient graft site. By using the methods, a specific sprayed cell suspension is defined.

According to the invention a method is provided for spraying a cell suspension through a controlled spray head suitable for application to a patient utilizing a spray device, which method comprises the steps of: (a) subjecting a tissue sample including cells suitable for grafting to a patient, to at least a physical and/or chemical dissociating means capable of dissociating cells in the tissue sample; (b) taking the cells suitable for grafting on to a patient into a physiological saline solution, (c) filtering the cellular suspension produced to remove large cellular conglomerates; and spraying the cell suspension through a spray head.

According to the invention an electronically controlled apparatus is provided as a medical device for distribution of tissue regenerating cells in a sterile suspension over a tissue surface via electronic controlled sterile gas/air flow and a syringe pump for a suspension. Spraying is enabled through a sterile needle leading the suspension, which is inserted into a sterile tube leading the gas, and by providing continuous flow application of gas along the needle with the suspension for generating suspension drops at the tip of the needle containing cells; in a single shot.

According to the invention there is provided a cell suspension produced according to the above-described method. Preferably the cells in the suspension are autologous cells (i.e. they are isolated from the patient requiring an autograft), or progenitor/stem cells.

According to another aspect of the invention a method is provided to treat a patient in need of graft surgery.

Other aspects and advantages of the invention will become apparent to those skilled in the art from a review of the ensuing description, which proceeds with reference to the following descriptions and drawings.

BRIEF DESCRIPTION OF DRAWINGS

FIG. 1 compares two application modes of skin cells to a patient. Application of the method and/or device described in this text at hand, spraying skin cells onto a skin wound surface, is illustrated. This is compared to the state of the art medical treatment with skin cell application using confluently grown keratinocyte sheets. Using sprayed cells results in the need of fewer cells while a larger treatment surface can be enabled for therapy. Blister formation is avoided by the use of single cells without forming a closed sheet. Reducing the cell number speeds up application time by avoiding an in vitro cell expansion. This reduces in vitro differentiation and therefore better preserves basal keratinoyte progenitor cells in the cell suspension.

FIG. 2 shows an example of an assembly of a syringe for a cell suspension on a hand held sprayer with a syringe motor and a gas/air line leading to an air tube-suspension needle assembly on the spray head. The principle of this assembly on the spray head is illustrated in FIG. 3.

FIG. 3 shows an example of the assembly of an air tube-injectionion needle on the spray head of a cell sprayer, as depicted in FIG. 2.

DRAWINGS

FIG. 1 A-C: Illustration of single cell spray transplantation versus sheet transplantation. A) Problem of blister formation under sheets. B) Larger surface treatment by spraying. C) No danger of blister formation after spraying.

FIG. 2: Example of assembly of a syringe on a hand held sprayer with in a syringe motor and a gas/air line leading to an air tube-suspension needle assembly on the spray head. The principle of is illustrated in FIG. 3.

FIG. 3: Example of assembly of an air tube-suspension needle assembly on the spray head of a cell sprayer, as depicted in FIG. 2.

DETAILED DESCRIPTION OF THE INVENTION

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification. Functionally equivalent products, compositions and where appropriate methods are within the scope of the invention as described herein.

Throughout this specification and the claims that follow, unless the context requires otherwise, the word “comprise”, or variations such as “comprises” or “comprising”, will be understood to imply the inclusion of a stated integer or group of integers but not the exclusion of any other integer or group of integers.

Having regard to the above, this invention provides a unique method and/or device suitable for producing a transplantable cellular suspension of living tissue suitable for grafting to a patient. In applying the method and/or in using the device, cell preparations of different origin may be used. This includes progenitor/stem cell preparations and patient autologous cells, whereas donor tissue is harvested and subjected to a tissue dissociating means. Cells suitable for grafting to a patient, or as an autograft back to a patient, are dispersed in a solution that is suitable for immediate dispersion over the recipient graft site.

The subject invention has many advantages over the prior art some of which are described in the following paragraphs.

1. It provides a time-efficient method for supplying a cellular cover to a tissue in a clinical setting. That is, cells are finely and evenly distributed over a wound, avoiding the use of cell sheets. In contrast to the use of spray nozzles a cells/suspension nebulization the is thought to injure cells can be avoided. This is achievable because there is a controlled procuring of the cell suspension through a medical grade cannulla with a method provided by an apparatus, thus allowing cell spraying to be performed more evenly than the mechanical hand operated methods of the prior state of the art.

2. It provides a method and an apparatus, which avoids the blister formation associated with the use of conventional CEA’s.

3. It aids in the achievement of rapid cell coverage in areas of tissue wounds, tissue trauma/injury and donor sites. It provides a means for reducing the size of skin cell donor sites—the biopsy donor site is markedly smaller than a split skin graft donor site and reduces or eliminates the use of split skin graft donor sites; improves the expansion rate of cell coverage; improves the rate of healing of small burns; is useful for small areas of skin reconstructions, such as scars; and improves scar quality.

4. It provides a means for the treatment of various skin disorders or diseases. For example, it may be used for the following: dermal resurfacinging, epidermal resurfacing, replacement after skin loss, site match-up during re-pigmentation of an area of skin, treatment of burn wounds, leukoderma, vitiligo, piebaldism, in the treatment of scars (for example caused through incorrect wound healing, improper scar direction or scar distortion from wound contraction, acne scars), resurfacing cosmetic dermabrasion, resurfacing after laser treatment and in association with dermal reconstruction. Additionally, the method may be used for cell replacement therapy, including, for example, nerve cell replacement treatment, epithelial cell (such as urothelial cell, buccal mucosal cell and respiratory epithelial cell) replacement treatment, endothelial cell replacement treatment and osteogenic precursor cell replacement treatment. The method/device may also be used to stimulate tissue regeneration in surgically induced wounds.

5. It provides a means to produce a suspension of various cells in a ratio to each other comparable with those seen in situ. That is, due to the manner of preparation of the cellular suspension, cells such as keratinocyte basal cells, Langerhans cells, fibroblasts and melanocytes typically have enhanced survival rates in comparison to standard tissue culture techniques, whereby selective cell culture can result in the loss of certain cell types. The use of all skin cell types has the advantage of allowing for the correct re-pigmentation of skin after a skin graft.

6. By enabling an intra-operative setting on site of wound treatment, it allows faster surgery and healing—thereby reducing trauma for patients during the phase of their medical care in situations awaiting the availability of 2-4 week cultured cells.

The invention relates to at least two distinct cell sources, all suitable for use in resurfacing and regeneration of damaged tissue: (i) non-autologous cells, including stem cells, and (ii) autologous cells, including the patient's own progenitor cells.

The invention provides a method for preparing an autologous cell suspension. According to this method, tissue is harvested from a patient by means known in the art of tissue grafting. Preferably this is achieved by taking a tissue biopsy. With the harvesting of the biopsy consideration must be given to the depth of the biopsy and size of the surface area. The depth and size of the biopsy influence the ease at which the procedure can be undertaken and the speed with which a patient recovers from the procedure. In a highly preferred form of the invention the chosen donor site should appropriately match the recipient site, for example post-auricular for head and neck, thigh for lower limbs, inner-upper-arm for upper limbs, or palm for sole or vice-versa.

Once a biopsy has been harvested from a patient the tissue sample is subjected to physical and/or chemical dissociating means capable of dissociating cellular stratum in the tissue sample. Methods for dissociating cellular layers within the tissues are well known in the field; see Johnen et al. (2006). For example, the dissociating means may be either a physical or a chemical disruption. Physical dissociation means might include, for example, scraping the tissue sample with a scalpel, mincing the tissue, physically cutting the layers apart, or perfusing the tissue. Chemical dissociation means might include, for example, digestion with enzymes such as trypsin, dispase, collagenase, trypsin-edta, thermolysin, pronase, hyaluronidase, elastase, papain and pancreatin. Non-enzymatic solutions for the dissociation of tissue can also be used. Preferably, dissociation of the tissue sample is achieved by placing the sample in a pre-warmed enzyme solution containing an amount of enzyme sufficient to dissociate cellular stratum in the tissue sample.

After the tissue sample has been immersed in the enzyme solution for an appropriate amount of time, the sample is removed and washed with nutrient solution.

The saline/nutrient solution used in the method should be capable of significantly reducing and more preferably removing the effect of the enzyme either by dilution or neutralization. The nutrient solution used in the method will also preferably have the characteristics of being (i) free of at least xenogenic serum, (ii) capable of maintaining the viability of the cells until applied to a patient, and (iii) suitable for direct application to a region on a patient undergoing tissue grafting. After application of a suitable saline/nutrition solution to the tissue sample, the cellular stratum of the sample is separated permitting the cells capable of reproduction to be removed from the cellular material and suspended in the nutrient solution. In case the tissue sample is skin, the dermis and epidermis of the skin biopsy are preferably separated to allow access to the dermal-epithelial junction of the basal epidermal layer.

Cells capable of reproduction are then removed from the separated stratum by any means known in the art. Preferably, the reproductive cells are scraped off the surface of the stratum using an instrument such as a scalpel. Cells capable of reproduction within the dermal-epithelial junction include but are not limited to keratinocyte basal cells, Langerhans cells, fibroblasts, mesenchymal stem cells, and melanocytes. Following release of the cells from the tissue sample they are suspended in the saline/nutrient solution.

These methods and their application to patients are well known, while different spray devices and spray methods were applied (see literature Wood et al. and Gerlach et al.)

The invention provides simultaneously a method for using a non-autologous cell suspension. To procure cells of any source, the cells are suspended in an aquaeus saline/nutrition solution. The solution may be anything physiological from a basic salt solution to a more complex buffer and/or nutrient solution. Preferably, the nutrient solution is free of all serum but contains various salts that resemble the substances found in body fluids; this type of solution is often called physiological saline. Phosphate or other non-toxic substances may also buffer the solution in order to maintain the pH at approximate physiological levels. Suitable nutrient solutions that are preferred base on Ringer-lactate solutions, including Hartmann's solution, dialysis solutions, and on peripheral intravenous nutrition solutions.

Preferably only a small volume of solution is applied to the tissue sample after the harvesting steps, or by suspending non-autologous cells, otherwise the suspension may become too fluid therein providing difficulties in applying the suspension to the graft.

The cell suspension is then applied by using the spray device, described in the claims.

To avoid excessively large cellular congregates in the cellular suspension the suspension is preferably filtered, either prior to using the suspension with the device, or by a specific feature of the device.

Prior to application with the device or immediately after filtering, the cellular suspension may be diluted to produce an appropriate cell density suitable for the purpose with which the suspension is to be used.

According to the invention there is provided a sprayed aqueous cell suspension, highly suitable for tissue regeneration and grafting techniques, produced by the method described. An important advantage of the invention is an even cell distribution.

An important aspect of utilizing such a suspension in grafting technology is that it can be used to greatly expand the area or volume of a wound that can be treated quickly by in situ multiplication of a limited number of cells. Cellular multiplication is encouraged on the patient rather than in an in vitro system, as provided by the state of the art CEA method.

The number and concentration of cells seeded onto graft site may be varied by modifying the concentration of cells in suspension, or by modifying the quantity of suspension that is distributed onto a given area or volume of the graft site.

Another unique feature of the cell suspension produced according to the method of the invention is that the composition of cells in the cellular preparation is comparable to that seen in situ compared to prior art CEA cellular preparation. Importantly, it contains the basal keratinocytes and skin progenitor cells for skin regeneration, which are typically lost in the CEA method. In this prior art, culture of the cellular preparation utilizes selective culture for keratinocytes, therefore the loss of cellular constituents such as skin progenitor cells, fibroblasts, mesenchymal stem cells, and melanocytes occurs, whereas the cellular suspension produced by the method of the invention has a cell composition comparable to the in situ cell population.

According to a further aspect of the invention there is provided a method of treatment of the patient requiring a tissue graft. By this method the cellular suspension produced according to the invention is applied to a graft site.

According to the invention there is provided an apparatus to distribute the cells. The suspension is sprayed through a needle/gas tube assembly that transforms a cell suspension into small airborne droplets. By adjusting the airstream and the liquid stream, the spray deposition can be varied and adapted to specific needs.

According to the invention there is provided an electronically controlled apparatus as a medical device to operate the spraying through a sterilizeable spray head assembly. Preferrably the apparatus enables a distribution of cells using a 0.5-60±20 ml sterile cell suspension through a spray head assembly. Preferrably, the apparatus transfers the cell suspension from a medical grade disposable sterilizeable syringe, including 0.5-60 ml sterile Luer-lock syringes, through the lumen of a preferably medical grade disposable sterile syringe needle.

The apparatus can be operated preferably basing based on producing compressed sterile filtered gas, e.g. air, for the tube in the spray head assembly and by motor operated pushing of the plunger of a syringe, preferably a sterile disposable Luer-look syringe, containing the cell suspension. The apparatus preferably provides continuous force application over a range of 0.5-10±1.0 minutes for in a single shot, or several shots, and generates suspension drops containing cells in the range of 30-500±200 micrometer.

The apparatus may provide means to measure and control parameters such as flow, pressure, volume and/or temperature.

The apparatus preferably also transfers the cell suspension from a medical grade sterilizeable container to the sterilizeable spray head via a disposable filter capable of separating large cellular congregates from a cellular suspension. Any filter capable of separating excessively large cellular congregates from the suspension may be used. In a highly preferred form of the invention the filter exhibits a cut off of approximately 5-100 cells, preferably 20-60 cells and most preferred 40 cells.

In further embodiments the apparatus can also support two or more liquid containers/syringes in parallel.

The apparatus may comprise a first and second member/element wherein: (i) the first element includes power supply, gas/air supply and electronic controls, and (ii) the second element includes a sterilizeable spray head and the container with the cell suspension. In that case both elements are connected through a cable/wire/tube sensor/effector connector which may be sterilizeable or can be covered with a sterile operation foil hose and has suitable connectors to the elements (i) and (ii).

The apparatus may comprise a first and second element wherein both elements are wirelessly connected for data exchange, including blue tooth technology, to connect sensor/effector controls in the first and second member.

The apparatus may also feature battery operation, facilitating an easy use in operation theaters. In that preferred case, the apparatus comprises an all-in one device for hand-held operation.

After the cell suspension has been applied to the recipient graft site, the wound may be covered with a wound dressing. Preferably, the healing of the wound is followed up by standard protocols for graft treatment known to those skilled in the art.

FIG. 2 shows a device 10 for controlled cell spraying. The device 10 can include a component 12, a handle 14, a user-operable control 16, a battery 18, an actuator 20, a filter housing 22, and a connector 24 for coupling with a supply of gas.

FIG. 3 shows an end of the component 12 of FIG. 2. The component 12 can include a spray head 30, a tube path 32, a needle path 38, and a needle 40. The tube path 32 can include a curved portion 34 and a discharge portion 36. FIG. 3 shows the needle path 38 intersecting the tube path 32 at the curved portion 34, whereby the needle 40 penetrates the tube in the tube path 32.

EXAMPLE

If not otherwise indicated, all materials were purchased from Biochrom AG, Berlin, Germany. Media were supplemented with antibiotics (Penicillin/Streptomycin, 120 μg/ml) and antimycotics (Amphotericin B, 2.5 μg/ml). A 1 $cm^2$ skin biopsy was obtained after obtaining informed consent of the donor and cut into 2 $mm^2$ pieces. The methods are described in more detail in Johnen et al. (2006). Prior to separation of epidermis and dermis the pieces were exposed to 0.4% dispase (Serva Electrophoresis GmbH, Heidelberg, Germany) in DMEM at 37° C. for 20-40 minutes. Various enzyme combinations were employed. Separated epidermis and dermis were each incubated with 0.05% trypsin/0.02% EDTA-solution for 10-20 minutes. From separated epidermis and dermis, the dermis was incubated with 0.05% trypsin/0.02% EDTA-solution for 10-20 minutes and used. While separated epidermis and dermis were each incubated with trypsin, the dermis was also incubated alternatively with collagenase in other cases. The single cell suspensions were washed and use or mixed together and used. They contained basal keratinocytes, melanocytes and dermal fibroblasts and mesenchymal stromal cells The suspension was cultivated in a standard culture flask with serum free culture medium (EpiLife, TEBU, Offenbach, Germany). Cells were incubated at a cell density of $10^4$ per $cm^2$, using a $CO_2$-incubator (Heraeus BB 6060, Kendro, Langenselbold, Germany) at 37° C. in a humidified atmosphere with 5% $CO_2$. Medium was changed every two days. As 80% confluence was reached, cells were detached by trypsinization and used with the above described spray device prototype. The cells were sprayed into a non medium filled standard cell culture dish at a density of $10^4$ cells per $cm^2$. As control cells from the same suspension were cultivated, under the above described culture conditions after pipetting into a medium filled culture flask with the same density. Cell morphology was monitored by light microscopy (Zeiss, Axiovert 25). Sprayed and non-sprayed cells showed similar morphologic appearance in light- and phase-contrast microscopy, they also showed comparable follow up culture behavior. Similar cell spray applications with a cell spray device that was developed earlier were published by Gerlach et al. J Artif Org 2011 March; 34(3):271-9.

Modifications and variations of the described methods and device of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant field in which this invention resides are intended to be within the scope of the described claims.

In an example, a device for controlled spraying of biological compatible liquids, biological compatible suspensions, and biological cell suspensions including stem cell suspensions, modified stem cell suspensions, cell suspensions for wound regeneration, cell suspensions for dermal cells, cell suspensions for epidermal cells, cell suspensions for dermal and epidermal cells, can include providing continuous spray application over a range of 0.5-10 minutes, preferably 1-2 minutes in a single shot and/or in several shots, while generating liquid/suspension drops ranging between 10-500 micrometer in size, exhibiting a hollow needle to deposit liquids/suspensions, which is connected at the outlet of a biocompatible container delivering a liquid/suspension stream towards the tip of the needle, injected with the tip into a biocompatible tube delivering a gas and/or air stream in direction to the end of the tube where the tip of the needle is positioned.

In an example, the needle exhibits an inner lumen of 25 G to 34 G, preferably of 27 G to 30 G.

In an example, the needle is injected into the tube in a way that the tip of the needle ends within +/–3 millimeter, preferably +/–0.2 millimeter at the end of the tube.

In an example, the tip of the needle runs within the tube at least 2-100 millimeter, preferably 4-20 millimeter in parallel to the tube so that the needle tip is centered in the end of the tube lumen.

In an example, the tube exhibits an inner diameter of 1.5-0.2 millimeter, preferably of 0.8-0.6 millimeter.

In an example, the tube bends at the point of needle injection with a radius not prohibiting the gas flow to the side in an angle of 1 degree-170 degree, preferably 80 degree-100 degree, enabling an easy needle injection.

In an example, the gas stream is preferably a gas/air mix stream, preferably a sterile-filtered air stream.

In an example, the device delivers via the needle a liquid/suspension stream of 1-200 mL/min, preferably 5-30 mL/min.

In an example, the device delivers via the tube a gas stream of 100-4000 mL/min, preferably 200-2000 mL/min.

In an example, the gas stream is generated by a compressed gas container, or a gas pump, preferably a compressor in the device or in a separate housing attached to the device via a tube preferably sterile-filtered prior to entering the needle, e.g. by a sterile-filter.

In an example, the liquid/suspension stream is generated by a compressible container, preferably by a syringe with plunger, which is connected to an actuator, including a pneumatic gas- or hydraulic liquid membrane, or an mechanical/electromechanical pusher, which pushes the plunger of the syringe to generate the liquid/suspension flow.

In an example, the device can be presented as a single, hand held mechanically and/or battery operated device, or a device out of at least 2 components with a handheld spray unit and a support unit including electric power supply which are connected via pneumatic/hydraulic/electric lines.

In an example, the above characterized needle/tube/operation parameter configuration produces a homogeneous and continuous spray stream generated by the flow of the liquid medium out of the tip and of the specific gaseous medium out of the tube, which is less cell suspension harmful than the typical cell spray nozzle using openings far below and turbulences far above the presented configuration.

In an example, either all hand held parts of the device are sterilized prior use, or only the parts containing gas and liquid/suspension streams are sterilized prior use, or whereas all liquid/gas transferring parts are delivered separately sterilized and are assembled in a sterile manner immediately prior to use.

In an example, the device can be embodied as a fully disposable device.

In an example, the device is embodied for insertion of disposable medical grade sterile syringes, including with Luer-lock connector, disposable medical grade sterile tubes, including with Luer-lock connectors, disposable medical grade sterile gas sterile-filters, including with Luer-lock connectors, disposable medical grade sterile suspension filters, including with Luer-lock connectors, disposable medical grade sterile needles, including with Luer-lock connector, whereas either all handheld non disposable parts of the device are pre-sterilized and all disposable sterile parts are assembled onto the handheld part in a sterile manner immediately prior to use, or all disposable sterile parts are assembled onto the handheld part in a sterile manner immediately prior to use after the device was covered with a sterile plastic hose/sheeting.

In an example, the device utilizes a solution as an aqueous solution containing electrolytes in a physiologic composition, including Ringer-Lactate like electrolyte solutions, including Hartman's solution.

In an example, the device transfers the cell suspension from a medical-grade sterilizeable container, including luer-lock syringes, to the sterilizeable spray needle/tube via a filter, preferable a disposable Luer-lock filter, capable of separating large cellular congregates with a cut off of approximately 5-100 cells, preferably 20-60 cells from a cellular suspension.

In an example, the device contains first and second components and has suitable connectors to the components (i) and (ii), wherein: (i) the first component includes the power supply, gas/air supply and electronic controls, and (ii) the second component includes the spray head and the container with the cell suspension; and wherein both components are connected through a cable/wire/tube sensor/effector connector; and wherein the second component and the connection between both components may be sterilizeable or can be covered with a sterile operation foil hose; wherein both components can be optionally wirelessly connected for electronic data exchange, including blue tooth technology to connect sensor/effector controls in the first and second component.

In an example, the device is embodied for the use of at least 2 consecutive applied container/syringes for dermal cells/progenitors followed by epidermal cells/progenitors by allowing to change the container/syringe.

In an example, the device is embodied for the use of at least 2 parallel applied container/syringes that contain different cells, including dermal cells/progenitors and epidermal cells/progenitors.

In an example, the device is embodied for the use of one applied container/syringes for a mix of cells, including dermal cells/progenitors and epidermal cells/progenitors.

In an example, the device contains sensors to measure flow and/or pressure, and/or temperature, and optionally feedback controls to control flow and/or pressure, and/or temperature.

In an example, the device is battery operated.

In an example, the device is fully mechanically driven, including with external gas/air source with pressure reducer and control, and/or mechanically powered syringe operation, and/or manual syringe operation.

In an example, a method of using the device described herein, for producing/using an autologous cell suspension for treating a patient in need of graft surgery, comprises the following steps: (a) preparing a cell suspension; and (b) administering the suspension directly to a region on the patient that requires a cell graft in a manner that facilitates spraying of the cell suspension in an even distribution over the graft area.

In an example, a method of using the device described herein, for producing/using a cell suspension for treating a patient in need of graft surgery with a cell suspension as described herein, includes administering the suspension to a region on the patient that requires a cell graft in a manner that facilitates spraying of the cell suspension in an even distribution over the graft area.

In an example, a method of using the device described herein, for coating an artificial surface or a biomaterial surface for research or commercial use with the device, comprises the following steps: (a) preparing a cell suspension, and (b) administering the suspension directly onto an artificial or a biomaterial that requires a cell coated surface in a manner that facilitates spraying of the cell suspension in an even distribution.

In an example, use of the device and methods described herein is for cell spraying/deposition/application in biomedical research and/or medicine.

In an example, a cell suspension can be produced using the device and methods described herein.

In an example, a cell suspension can be produced from in vitro expanded or non-cultured autologous cell and/or progenitor cell preparation, and/or in vitro expanded progenitor cells.

In an example, a cell suspension can be produced from in vitro expanded or non-cultured autologous or expanded non-autologous mesenchymal adult progenitor cell and adult basal keratinocyte progenitor cell preparations.

In an example, a cell suspension can be produced from in vitro expanded or non-cultured autologous basal keratinocyte or progenitor cell preparations in combination with non-autologous cultured mescenchymal stem cell preparations.

The invention claimed is:

1. A cell spray gun comprising:
    a component having a reservoir support portion configured to receive a reservoir containing a cell suspension, the component having a needle path and a tube path, the needle path aligned with the reservoir support portion and having an end terminating at a spray head, the tube path having a curved portion and a discharge portion, the discharge portion aligned coaxially with the needle path, and wherein the needle path intersects with the curved portion;
    a tube disposed within the tube path, an end portion of the tube disposed within the discharge portion;
    a hollow needle disposed within the needle path and coupleable with the reservoir at a first end of the needle to deliver the cell suspension to a second end of the needle, and wherein a wall of the tube is penetrated by the needle, and the second end of the needle is disposed within the end portion of the tube at the spray head for spraying the cell suspension;
    an actuator coupled to the component, the actuator having a plunger driver configured for linear motion relative to the reservoir support portion;
    a handle coupled to the component; and
    a user-operable control coupled to the handle wherein the actuator is operable in response to the control.

2. The cell spray gun of claim 1 further including a filter housing coupled to the tube path.

3. The cell spray gun of claim 1 wherein the reservoir includes a syringe body connectable to the needle.

4. The cell spray gun of claim 1 wherein the tube is a sterilizable tube.

5. The cell spray gun of claim 1 wherein the reservoir includes a syringe with a medical grade Luer-lock.

6. The cell spray gun of claim 1 wherein the user-operable control is configured to operate the actuator over a continuous period of 0.5-10 minutes.

7. The cell spray gun of claim 1 wherein the user-operable control is configured to operate the actuator over a single shot period of duration 0.5-10 minutes.

8. The cell spray gun of claim 1 wherein the spray head is configured to generate drops having a size in the range of 10-500 micrometer.

9. The cell spray gun of claim 1 wherein the tube path includes a connector for coupling the tube with a supply of gas.

10. The cell spray gun of claim 1 wherein the tube has an inner diameter of 1.5-0.2 mm.

11. The cell spray gun of claim 1 wherein the tube has an inner diameter of 0.8-0.6 mm.

12. The cell spray gun of claim 1 wherein the needle has a lumen of 25 G to 34 G.

13. The cell spray gun of claim 1 wherein the needle has a lumen of 27 G to 30 G.

14. The cell spray gun of claim 1 wherein the discharge portion has a length of less than 100 mm.

15. The cell spray gun of claim 1 wherein the discharge portion has a length of less than 20 mm.

16. The cell spray gun of claim 1 wherein the spray head is configured to provide a stream of 1-200 mL/min.

17. The cell spray gun of claim 1 wherein the spray head is configured to provide a stream of 5-30 mL/min.

18. The cell spray gun of claim 1 wherein the actuator includes at least one of a pneumatic actuator, a gas actuator, an hydraulic liquid membrane, or a mechanical/electromechanical actuator.

19. The cell spray gun of claim 1 further including a battery coupled to at least one of the actuator and the user-operable control.

* * * * *